US009587025B2

(12) United States Patent
Ravetch et al.

(10) Patent No.: US 9,587,025 B2
(45) Date of Patent: Mar. 7, 2017

(54) NON-SIALYLATED ANTI-INFLAMMATORY POLYPEPTIDES

(71) Applicant: THE ROCKEFELLER UNIVERSITY, New York, NY (US)

(72) Inventors: Jeffrey V. Ravetch, New York, NY (US); Andrew Pincetic, New York, NY (US)

(73) Assignee: The Rockefeller University, New York, NY (US)

(*) Notice: Subject to any disclaimer, the term of this patent is extended or adjusted under 35 U.S.C. 154(b) by 3 days.

(21) Appl. No.: 14/368,701

(22) PCT Filed: Dec. 10, 2012

(86) PCT No.: PCT/US2012/068718

§ 371 (c)(1),
(2) Date: Jun. 25, 2014

(87) PCT Pub. No.: WO2013/095966

PCT Pub. Date: Jun. 27, 2013

(65) Prior Publication Data

US 2014/0377280 A1 Dec. 25, 2014

Related U.S. Application Data

(60) Provisional application No. 61/577,361, filed on Dec. 19, 2011.

(51) Int. Cl.
*A61K 39/00* (2006.01)
*C07K 16/28* (2006.01)
(Continued)

(52) U.S. Cl.
CPC .......... *C07K 16/2851* (2013.01); *C07K 16/00* (2013.01); *C07K 16/08* (2013.01); *A61K 2039/505* (2013.01); *C07K 2317/41* (2013.01); *C07K 2317/52* (2013.01); *C07K 2317/72* (2013.01); *C07K 2318/00* (2013.01)

(58) Field of Classification Search
None
See application file for complete search history.

(56) References Cited

U.S. PATENT DOCUMENTS 8,188,231 B2 5/2012 Lazar et al.
2006/0153838 A1* 7/2006 Watkins et al. ............ 424/133.1
(Continued)

FOREIGN PATENT DOCUMENTS

JP 2008539753 A 11/2008
KR WO 2008147143 A2 * 12/2008 ............ C12N 15/62
(Continued)

OTHER PUBLICATIONS

Ha et al., "Isolation and characterization of IgG1 with asymmetrical Fc glycosylation," Glycobiology, vol. 21, No. 8: 1087-1096 (2011).*
(Continued)

*Primary Examiner* — Janet L Andres
*Assistant Examiner* — M. Franco Salvoza
(74) *Attorney, Agent, or Firm* — Fox Rothschild LLP

(57) ABSTRACT

This invention concerns anti-inflammatory agents, compositions, and methods for treating inflammatory disorders.

7 Claims, 11 Drawing Sheets

(51) Int. Cl.
*C07K 16/00* (2006.01)
*C07K 16/08* (2006.01)

(56) References Cited

U.S. PATENT DOCUMENTS

| | | | | |
|---|---|---|---|---|
| 2010/0172911 A1* | 7/2010 | Naso | C07K 16/00 | 424/141.1 |
| 2010/0286067 A1 | 11/2010 | DeFrees | | |
| 2012/0258041 A1* | 10/2012 | Basi | A61K 51/1018 | 424/1.49 |
| 2014/0112914 A1* | 4/2014 | Nezu | C07K 16/30 | 424/133.1 |

FOREIGN PATENT DOCUMENTS

| | | |
|---|---|---|
| WO | 2007039818 A2 | 4/2007 |
| WO | 2008076487 A2 | 6/2008 |
| WO | 2011059684 A1 | 5/2011 |

OTHER PUBLICATIONS

Jassal et al., "Sialylation of Human IgG-Fc Carbohydrate by Transfected Rat α2,6-Sialyltransferase," Biochemical and Biophysical Research Communications 286: 243-249 (2001).*
Anthony et al., "A Novel Role for the IgF Fc Glycan: The Anti-inflammatory Activity of Sialylated IgG Fcs," J Clin Immunol 30 (Suppl 1): S9-S14 (2010).*
Kaneko et al., "Anti-inflammatory Activity of Immunoglobulin G Resulting from Fc Sialylation," Science, vol. 313:670 (2006).*
Scallon et al., "Higher levels of sialyated Fc glycans in immunoglobulin G molecules can adversely impact functionality," Molecular Immunology 44: 1524-1534 (2007).*
Igawa et al., "Engineering the variable region of therapeutic IgG antibodies," mAbs 3:3: 243-252 (2011).*
Lefevre et al., "Alanine-stretch scanning mutagenesis: a simple and efficient method to probe protein structure and function," Nucleic Acids Research, vol. 25, No. 2: 447-448 (1997).*
Rudikoff et al. ("Single amino acid substitution altering antigen-binding specificity," Proc Natl Acad Sci USA 79:1979-1983 (1982).*
Ahmed et al., "Structural Characterization of Anti-Inflammatory Irnmunoglobulin G Fc Proteins," Journal of Molecular Biology (Sep. 1, 2014): 426(18):3166-3179.
Anthony et al., "Recapitulation of IVIG anti-inflammatory activity with a recombinant IgG Fc," Science (Apr. 18, 2008): 320(5874):373-376.
Campell et al., Therapeutic Effect of IV1G on Inflammatory Arthritis in Mice is Dependent on the Fc Portion and Independent of Sialylation or Basophils, The Journal of Immunology (Apr. 23, 2014); 192(11):5031-5038.
Lund et al., "Multiple Interactions of IgG with its Core Oligosaccharide Can Modulate Recognition by Complement and Human Fc gamma Receptor I and influence the Synthesis of its Oligosaccharide Chains." The Journal of Immunology (Dec. 1, 1996); 157(11):4963-4969.
Stadlmann et al., Analytical and Functional Aspects of Antibody Sialylation, Journal of Clinical Immunology (May 1, 2010); 30(Supp. 1):S15-S19.
Stadlmann et al., "A Close Look at Human IgG Sialylation and Subclass Distribution After Lectin Fractionation," Proteomics (Sep. 1, 2009); 9(17):4143-4153.
Yu et al., "Engineering Hydrophobic Protein-Carbohydrate Interactions to Fine-Tune Monoclonal Antibodies," Journal of the American Chemical Society, (Jul. 3, 2013); 135(26):9723-9732.
Burton et al. "Sugar Determnies Antibody Activity," Science (Aug. 4, 2006):313:627-628.
Ramakrishna et al., "Passively Administered Pooled Human Immunoglobulins Exert IL-10 Dependent Anti-Inflammatory Effects That Protect Against Fatal HSV Encephalitis," PLoS Pathog. (Jun. 2, 2011):7(6):1-17.

* cited by examiner

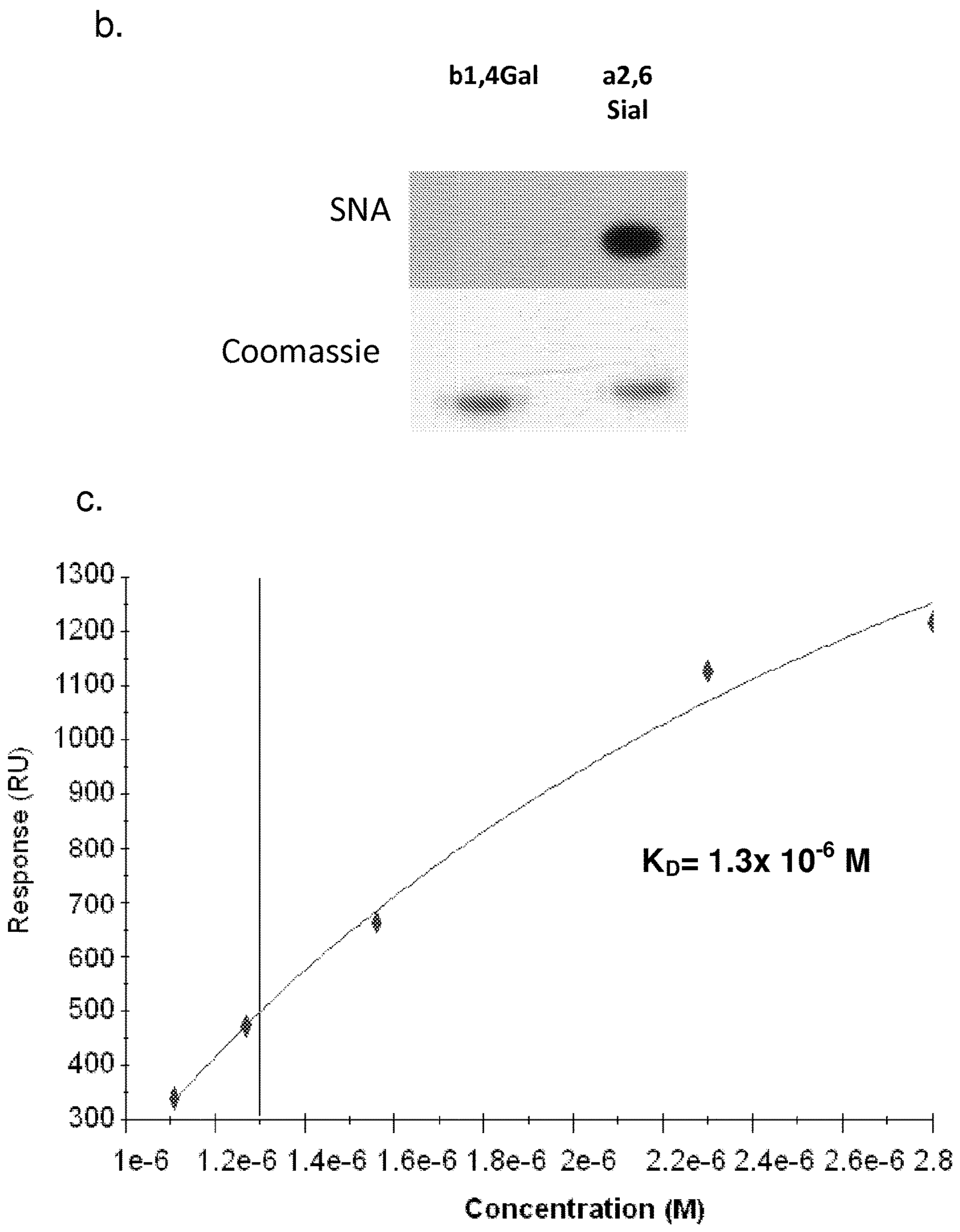
FIGURES 1 B-C

SEQUENCE LISTING

```
<160> NUMBER OF SEQ ID NOS: 9

<210> SEQ ID NO 1
<211> LENGTH: 238
<212> TYPE: PRT
<213> ORGANISM: Homo sapiens

<400> SEQUENCE: 1

Lys Val Asp Lys Arg Val Glu Pro Lys Ser Cys Asp Lys Thr His Thr
1               5                   10                  15

Cys Pro Pro Cys Pro Ala Pro Glu Leu Leu Gly Gly Pro Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95
```

-continued

```
Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235


<210> SEQ ID NO 2
<211> LENGTH: 238
<212> TYPE: PRT
<213> ORGANISM: Artificial Sequence
<220> FEATURE:
<223> OTHER INFORMATION: FA241 Mutant

<400> SEQUENCE: 2

Lys Val Asp Lys Arg Val Glu Pro Lys Ser Cys Asp Lys Thr His Thr
1               5                   10                  15

Cys Pro Pro Cys Pro Ala Pro Glu Leu Leu Gly Gly Pro Ser Val Ala
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220
```

-continued

Asn His Tyr Thr Gln Lys Ser Leu Ser Leu Ser Pro Gly Lys
225 230 235

<210> SEQ ID NO 3
<211> LENGTH: 238
<212> TYPE: PRT
<213> ORGANISM: Artificial Sequence
<220> FEATURE:
<223> OTHER INFORMATION: FA243 Mutant

<400> SEQUENCE: 3

Lys Val Asp Lys Arg Val Glu Pro Lys Ser Cys Asp Lys Thr His Thr
1 5 10 15

Cys Pro Pro Cys Pro Ala Pro Glu Leu Leu Gly Gly Pro Ser Val Phe
20 25 30

Leu Ala Pro Pro Lys Pro Lys Asp Thr Leu Met Ile Ser Arg Thr Pro
35 40 45

Glu Val Thr Cys Val Val Val Asp Val Ser His Glu Asp Pro Glu Val
50 55 60

Lys Phe Asn Trp Tyr Val Asp Gly Val Glu Val His Asn Ala Lys Thr
65 70 75 80

Lys Pro Arg Glu Glu Gln Tyr Asn Ser Thr Tyr Arg Val Val Ser Val
85 90 95

Leu Thr Val Leu His Gln Asp Trp Leu Asn Gly Lys Glu Tyr Lys Cys
100 105 110

Lys Val Ser Asn Lys Ala Leu Pro Ala Pro Ile Glu Lys Thr Ile Ser
115 120 125

Lys Ala Lys Gly Gln Pro Arg Glu Pro Gln Val Tyr Thr Leu Pro Pro
130 135 140

Ser Arg Asp Glu Leu Thr Lys Asn Gln Val Ser Leu Thr Cys Leu Val
145 150 155 160

Lys Gly Phe Tyr Pro Ser Asp Ile Ala Val Glu Trp Glu Ser Asn Gly
165 170 175

Gln Pro Glu Asn Asn Tyr Lys Thr Thr Pro Pro Val Leu Asp Ser Asp
180 185 190

Gly Ser Phe Phe Leu Tyr Ser Lys Leu Thr Val Asp Lys Ser Arg Trp
195 200 205

Gln Gln Gly Asn Val Phe Ser Cys Ser Val Met His Glu Ala Leu His
210 215 220

Asn His Tyr Thr Gln Lys Ser Leu Ser Leu Ser Pro Gly Lys
225 230 235

<210> SEQ ID NO 4
<211> LENGTH: 30
<212> TYPE: DNA
<213> ORGANISM: Artificial Sequence
<220> FEATURE:
<223> OTHER INFORMATION: PCR Primer

<400> SEQUENCE: 4
ggggaccgtc agtcgccctc ttccccccaa 30

<210> SEQ ID NO 5
<211> LENGTH: 30
<212> TYPE: DNA
<213> ORGANISM: Artificial Sequence
<220> FEATURE:
<223> OTHER INFORMATION: PCR Primer

<400> SEQUENCE: 5

-continued

```
ttggggggaa gagggcgact gacggtcccc                                         30


<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6

gaagatccca acagaagacc                                                    20


<210> SEQ ID NO 7
<211> LENGTH: 20
<212> TYPE: DNA
<213> ORGANISM: Artificial Sequence
<220> FEATURE:
<223> OTHER INFORMATION: PCT Primer

<400> SEQUENCE: 7

ttccggaggc gagacgtcac                                                    20


<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8

gccgcctgga gaaacctgc                                                     19


<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9

tgaggtccac caccctgttg                                                    20
```

NON-SIALYLATED ANTI-INFLAMMATORY POLYPEPTIDES

CROSS REFERENCE TO RELATED APPLICATIONS

This application is a U.S. National Phase based on International Application No. PCT/US2012/068718, filed Dec. 10, 2012, which claims priority of U.S. Provisional Application No. 61/577,361, filed on Dec. 19, 2011. The contents of the applications are incorporated herein by reference in their entirety.

GOVERNMENT INTERESTS

The invention disclosed herein was made, at least in part, with Government support under Grant No. NIH AI035875 from the National Institutes of Health. Accordingly, the U.S. Government has certain rights in this invention.

FIELD OF INVENTION

This invention relates to anti-inflammatory agents, compositions, and methods for treating inflammatory disorders.

BACKGROUND

Inflammatory disorders, including autoimmune diseases, are disorders involving abnormal activation and subsequent migration of white blood cells to affected areas of the body. These conditions encompass a wide range of ailments that affect the lives of millions of people throughout the world. Although various treatments are presently available, many possess significantly side effects or are not very effective in alleviating all symptoms. Thus, there are needs for anti-inflammatory agents for treating inflammatory disorders and needs for methods of identifying and evaluating such agents.

Immunoglobulin G (IgG) has long been appreciated to mediate both pro- and anti-inflammatory activities through interactions mediated by its Fc fragment. While Fc-FcγR interactions are responsible for the pro-inflammatory properties of immune complexes and cytotoxic antibodies, intravenous gamma globulin (IVIG) and its Fc fragments are anti-inflammatory and are widely used to suppress inflammatory diseases. It has been proposed that glycosylation of IgG is crucial for regulation of cytotoxicity and inflammatory potential of IgG. For example, it has been suggested that anti-inflammatory activity of IVIG is a property of the Fc fragment and its linked glycan, requiring terminal α.2,6 sialic acid linkages, indicating a combined requirement for the specific polypeptide backbone and glycan structure for immunosuppression. (Anthony, et al., 2008, Science 320: 373-376 and WO 2007/117505).

However, only a minor population of IgG in IVIG have glycans terminating in α2,6 sialic acids (sFc) and the anti-inflammatory activity. As a result, for the suppression of autoantibody triggered inflammation in a variety of clinical settings, one has to administer IVIG at high doses (1-2 g/kg), to enrich sialylated IgGs, or otherwise to increase the sialylation of IgGs (US Application Nos. 20080206246, and 20090004179, and Nimmerjahn et al. *Annu Rev Immunol* 26, 513-533 (2008)).

The present invention addresses and meets the above-mentioned needs by identifying sialylation-free anti-inflammatory polypeptides.

SUMMARY

This invention relates to agents, such as polypeptides and antibodies, and methods for treating inflammatory disorders, e.g., autoimmune diseases.

Accordingly, one aspect of this invention features an isolated polypeptide comprising a modified sequence that is at least 75% (e.g., any number between 75% and 100%, inclusive, e.g., 70%, 80%, 85%, 90%, 95%, 99%, and 100%) identical to an IgG Fc region. The modified sequence is free of sialylation and the polypeptide has an anti-inflammatory activity that is higher than that of a parent polypeptide. The parent polypeptide can comprise the IgG Fc region, such as the sequence of SEQ ID NO: 1 listed below. In some embodiments, the polypeptide has ability to bind to DC-SIGN, and to bind to hFcγRIIA or RIIB In one embodiment, the isolated polypeptide has an ability to bind to hFcγRIIA or RIIB at a $K_D$ of $2\times10^{-5}$ M or lower (i.e., $K_A$ of $5.0\times10^{4}$ $M^{-1}$ or higher). Preferably, the modified sequence has a FA241 mutation. The modified sequence can be at least 75% (e.g., any number between 75% and 100%, inclusive, e.g., 70%, 80%, 85%, 90%, 95%, 99%, and 100%) identical to SEQ ID NO: 2. In some examples, the modified sequence comprises or consists essentially of SEQ ID NO: 2.

In another aspect, the invention provides a method for making a polypeptide having an anti-inflammatory activity. The method includes, among others, steps of providing a parent polypeptide having the sequence of an IgG Fc region or a first nucleic acid sequence encoding the parent polypeptide; and modifying the parent polypeptide to obtain a modified polypeptide so that the modified polypeptide is free of sialylation and mimics the structural of a sialylated form of the IgG Fc region. The modifying step can be conducted by modifying the first nucleic acid sequence to obtain a second nucleic acid encoding the modified polypeptide. The invention also provides a polypeptide made by the just-described method.

In a third aspect, the invention features an isolated nucleic acid comprising a sequence encoding the polypeptide described above; an expression vector comprising the nucleic acid; and a host cell comprising the nucleic acid. The invention also features a method of producing a polypeptide. The method includes culturing the host cell in a medium under conditions permitting expression of a polypeptide encoded by the nucleic acid, and purifying the polypeptide from the cultured cell or the medium of the cell.

In a fourth aspect, the invention features a pharmaceutical formulation comprising (i) the polypeptide or nucleic acid described above, and (ii) a pharmaceutically acceptable carrier.

In a fifth aspect, the invention provides a method of treating an inflammatory disease. The method includes administering to a subject in need thereof a therapeutically effective amount of the above-described polypeptide or nucleic acid encoding the polypeptide. Also provided is use of the polypeptide or nucleic acid in the manufacture of a medicament for treating an inflammatory disease. The invention also features an isolated polypeptide, nucleic acid, expression vector, host cell, composition, or method for treating an inflammatory disease substantially as shown and described herein.

The details of one or more embodiments of the invention are set forth in the description below. Other features, objects, and advantages of the invention will be apparent from the description and from the claims.

DETAILED DESCRIPTION

Figure 1:
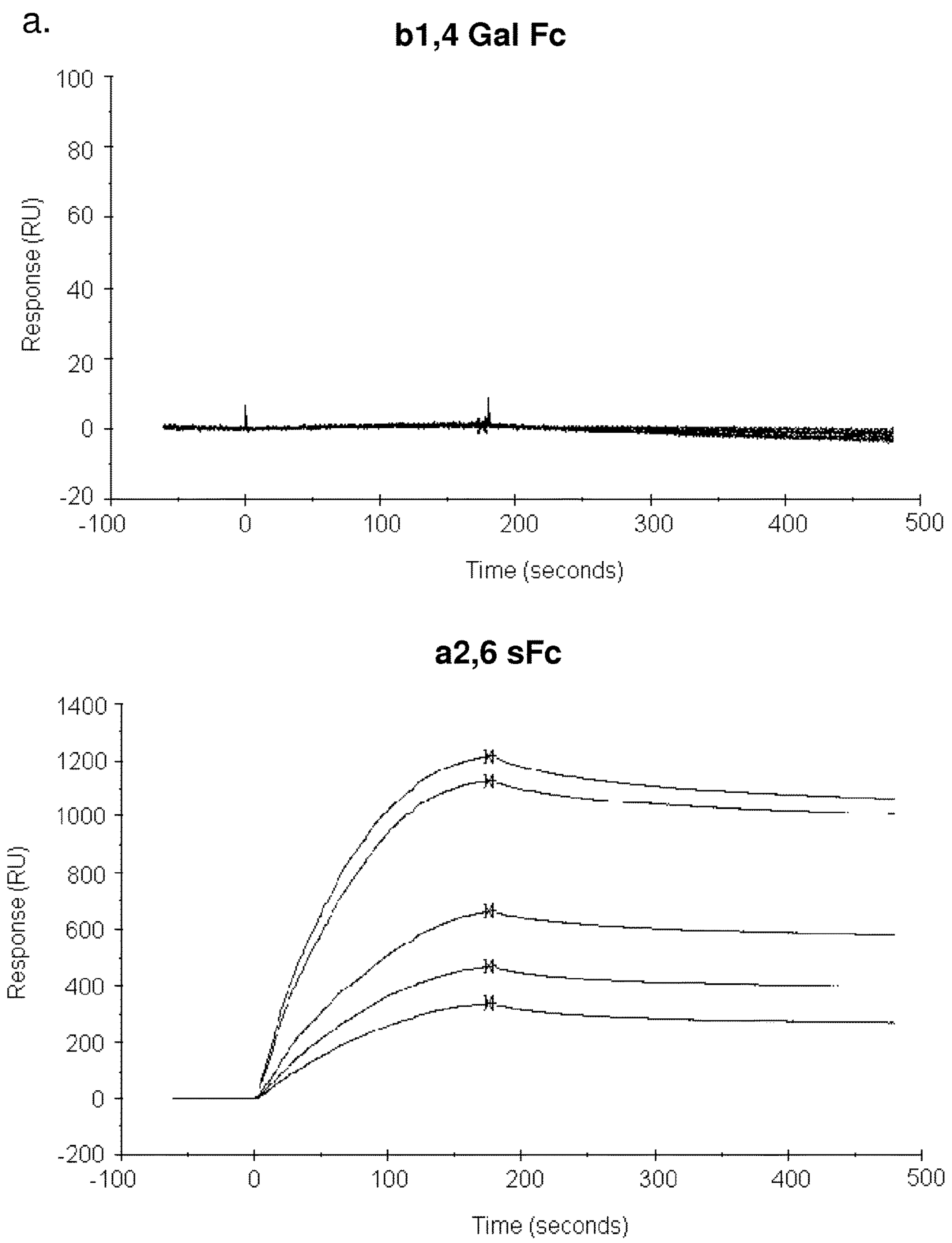
FIGS. 1a-c are diagrams and photographs showing that α2,6-linked sialic acid conferred DC-SIGN binding activity to recombinant human IgG1 Fc.

This invention is based, at least in part, on an unexpected discovery that non-sialylated IgG Fc variants confer anti-inflammatory activity and mimic the effect of 2,6 sialylated Fc as anti-inflammatory mediators.

IgG and Fc Sialylation

IgG is the major serum immunoglobulin. It is a glycoprotein composed of two identical heavy chains and two light chains, which in turn are composed of variable and constant domain. IgG contains a single, N-linked glycan at $Asn^{297}$ in the CH2 domain on each of its two heavy chains. The covalently-linked, complex carbohydrate is composed of a core, biantennary penta-polysaccharide containing N-acetylglucosamine (GlcNAc) and mannose (man). Further modification of the core carbohydrate structure is observed in serum antibodies with the presence of fucose, branching GlcNAc, galactose (gal) and terminal sialic acid (sa) moieties variably found. Over 40 different glycoforms have thus been detected to be covalently attached to this single glycosylation site (Fujii et al., J. Biol. Chem. 265, 6009, 1990). Glycosylation of IgG has been shown to be essential for binding to all FcyRs by maintaining an open conformation of the two heavy chains. Jefferis and Lund, Immune. 1 Lett. 82, 57 (2002), Sondermann et al., J. Mol. Biol. 309, 737 (2001). It is believed that this IgG glycosylation for FcyR binding accounts for the inability of deglycosylated IgG antibodies to mediate in vivo triggered inflammatory responses, such as ADCC, phagocytosis and the release of inflammatory mediators. Nimmerjahn and Ravetch, Immunity 24, 19 (2006). Further observations that individual glycoforms of IgG may contribute to modulating inflammatory responses has been suggested by the altered affinities for individual FcyRs reported for IgG antibodies containing or lacking fucose and their consequential affects on cytotoxicity. Shields et al., J. Biol. Chem. 277, 26733 (2002), Nimmerjahn and Ravetch, Science 310, 1510 (2005). A link between autoimmune states and specific glycosylation patterns of IgG antibodies has been observed in patients with rheumatoid arthritis and several autoimmune vasculities in which decreased galactosylation and sialylation of IgG antibodies have been reported. Parekh et al., Nature 316, 452 (1985), Rademacher et al., Proc. Natl. Acad. Sci. USA 91, 6123 (1994), Matsumoto et al., 128, 621 (2000), Holland et al., Biochim. Biophys. Acta December 27. Variations in IgG glycoforms have also been reported to be associated with aging and upon immunization, although the in vivo significance of these alterations have not been determined. Shikata et al., Glycoconj. J. 15, 683 (1998), Lastra, et al., Autoimmunity 28, 25 (1998).

As disclosed herein, certain non-sialylated IgG Fc variants surprisingly also confer anti-inflammatory activity. Such variants, including the FA241 variant, represent species within a larger genus of molecules that, by virtue of mimicking the structural and biological properties of sialylated Fc, but do not require sialylation, can be developed as anti-inflammatory therapeutics.

Polypeptides and Nucleic Acids

Polypeptides

As disclosed herein, this invention provides isolated polypeptides having sequences of variants of human IgG Fc that lacks a polysaccharide chain having a terminal sialic acid connected to a galactose moiety through the α2,6 linkage at the aforementioned $Asn^{297}$. Such non-sialylated IgG Fc variants may be either derived from a naturally occurring antibody or expressed in a cell line.

In one embodiment, the Fc region includes one or more substitutions of the hIgG1 amino acid sequence. While not limited thereto, exemplary IgG1 Fc regions are provided as follows:

```
Fc of hIgG1 (starting from amino acid 210 in
Kabat system):
KVDKRVEPKSCDKTHTCPPCPAPELLGGPSVFLFPPKPKDTLMIS

RTPEVTCVVVDVSHEDPEVKFNWYVDGVEVHNAKTKPREEQYNST

YRVVSVLTVLHQDWLNGKEYKCKVSNKALPAPIEKTISKAKGQPR

EPQVYTLPPSRDELTKNQVSLTCLVKGFYPSDIAVEWESNGQPEN

NYKTTPPVLDSDGSFFLYSKLTVDKSRWQQGNVFSCSVMHEALHN

HYTQKSLSLSPGK

(SEQ ID NO: 1; F241 and F243 are underlined)

Fc of hIgG1 FA241:
                                    (SEQ ID NO: 2)
KVDKRVEPKSCDKTHTCPPCPAPELLGGPSVALFPPKPKDTLMIS

RTPEVTCVVVDVSHEDPEVKFNWYVDGVEVHNAKTKPREEQYNST

YRVVSVLTVLHQDWLNGKEYKCKVSNKALPAPIEKTISKAKGQPR

EPQVYTLPPSRDELTKNQVSLTCLVKGFYPSDIAVEWESNGQPEN

NYKTTPPVLDSDGSFFLYSKLTVDKSRWQQGNVFSCSVMHEALHN

HYTQKSLSLSPGK

Fc of hIgG1 FA243:
                                    (SEQ ID NO: 3)
KVDKRVEPKSCDKTHTCPPCPAPELLGGPSVFLAPPKPKDTLMIS

RTPEVTCVVVDVSHEDPEVKFNWYVDGVEVHNAKTKPREEQYNST

YRVVSVLTVLHQDWLNGKEYKCKVSNKALPAPIEKTISKAKGQPR

EPQVYTLPPSRDELTKNQVSLTCLVKGFYPSDIAVEWESNGQPEN

NYKTTPPVLDSDGSFFLYSKLTVDKSRWQQGNVFSCSVMHEALHN

HYTQKSLSLSPGK
```

The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (for example, glycosylation or phosphorylation).

The peptide, polypeptide, or protein "of this invention" include recombinantly or synthetically produced versions having the particular domains or portions that bind to DC-SIGN, FcγRIIA, and FcγRIIB. The term also encompasses polypeptides that have an added amino-terminal methionine (useful for expression in prokaryotic cells).

An "isolated" polypeptide or protein refers to a polypeptide or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein described in the invention can be purified from a natural source, produced by recombinant DNA techniques, or by chemical methods. A functional equivalent of IgG Fc refers to a polypeptide derivative of IgG Fc, e.g., a protein having one or more point mutations, insertions, deletions, truncations, a fusion protein, or a combination thereof. It retains substantially the activity of the IgG Fc, i.e., the ability to bind to the respective receptor and trigger the respective cellular response. The isolated polypeptide can contain SEQ ID NO: 2. In general, the functional equivalent is at least 75% (e.g., any number between 75% and 100%, inclusive, e.g., 70%, 80%, 85%, 90%, 95%, and 99%) identical to SEQ ID NO: 2.

The "percent identity" of two amino acid sequences or of two nucleic acids is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST nucleotide searches can be performed with the NBLAST program, score=100, wordlength-12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

The amino acid composition of the polypeptide described herein may vary without disrupting the ability of the polypeptide to bind to the respective receptor and trigger the respective cellular response. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in, e.g., SEQ ID NO: 2, is preferably replaced with another amino acid residue from the same side chain family. Alternatively, mutations can be introduced randomly along all or part of the sequences, such as by saturation mutagenesis, and the resultant mutants can be screened for the ability to bind to the respective receptor and trigger the respective cellular response to identify mutants that retain the activity as descried below in the examples.

A polypeptide as described in this invention can be obtained as a recombinant polypeptide. To prepare a recombinant polypeptide, a nucleic acid encoding it (e.g., FA241, SEQ ID NO: 2) can be linked to another nucleic acid encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

Nucleic Acids

Another aspect of the invention features an isolated nucleic acid comprising a sequence that encodes the polypeptide or protein described above. A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" refers to a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the fusion protein of this invention. For this purpose, one can operatively linked the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector includes a nucleic acid in a form suitable for expression of the nucleic acid in a host cell. Preferably the vector includes one or more regulatory sequences operatively linked to the nucleic acid sequence to be expressed.

A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein or RNA desired, and the like. The expression vector can be introduced into host cells to produce a polypeptide of this invention. A promoter is defined as a DNA sequence that directs RNA polymerase to bind to DNA and initiate RNA synthesis. A strong promoter is one which causes mRNAs to be initiated at high frequency.

Any polynucleotide as mentioned above or a biologically equivalent polynucleotide available to the artisan for the same intended purpose may be inserted into an appropriate expression vector and linked with other DNA molecules to form "recombinant DNA molecules" expressing this receptor. These vectors may be comprised of DNA or RNA; for most cloning purposes DNA vectors are preferred. Typical vectors include plasmids, modified viruses, bacteriophage and cosmids, yeast artificial chromosomes and other forms of episomal or integrated DNA. It is well within the purview of the artisan to determine an appropriate vector for a particular use.

A variety of mammalian expression vectors may be used to express the above-mentioned IgG Fcs in mammalian cells. As noted above, expression vectors can be DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. Expression vectors may include, but are not limited to, cloning vectors, modified cloning vectors, specifically designed plasmids or viruses. Commercially available mammalian expression vectors which may be suitable, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAIamp (Invitrogen), pcDNA3 (Invitrogen), pMClneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

Also within the scope of this invention is a host cell that contains the above-described nucleic acid. Examples include *E. coli* cells, insect cells (e.g., using baculovirus expression vectors), yeast cells, or mammalian cells. See e.g., Goeddel, (1990) Gene Expression Technology: Methods in Enzymology 185, Academic Press, San Diego, Calif. To produce a polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, e.g., using T7 promoter regulatory sequences and T7 polymerase.

All of naturally occurring IgG Fcs, genetic engineered IgG Fcs, and chemically synthesized IgG Fcs can be used to practice the invention disclosed therein. IgG Fc obtained by recombinant DNA technology may have the same amino acid sequence as [FA241] SEQ ID NO: 2) or an functionally equivalent thereof. The term "IgG Fc" also covers chemically modified versions. Examples of chemically modified IgG Fc include IgG Fcs subjected to conformational change, addition or deletion of a sugar chain, and IgG Fc to which a compound such as polyethylene glycol has been bound.

One can verify the efficacy of a polypeptide/protein thus-made using an animal model, such as a transgenic mouse, as described below. Any statistically significant increase in in vivo expression of IL-33 basophils or expression of the FcγRIIB receptor on effector macrophages indicates the polypeptide/protein is a candidate for treating the disorders mentioned below. In one embodiment, the above described assays may based on measurement of a binding to DC-SIGN protein or DC-SIGN$^{(+)}$ cells. The art is replete with various techniques available to the artisan that will be suitable to measuring the ability of a compound to a DC-SIGN or to DC-SIGN$^{(+)}$ cells and related changes in expression of a gene regulated by the DC-SING pathway, such as IL-33. The artisan will be capable of mixing and matching these various research tools without undue experimentation. Once purified and tested by standard methods or according to the assays and methods described in the examples below, non-sialylated IgG Fc variants can be included in pharmaceutical composition for treating inflammatory disorders.

As used herein, "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, "antibody fragments", may comprise a portion of an intact antibody, generally including the antigen binding or variable region of the intact antibody or the Fc region of an antibody which retains FcR binding capability. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

As used herein, the term "Fc fragment" or "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

A "native sequence Fc region" comprises an amino acid sequence identical to the amino acid sequence of an Fc region found in nature. A "variant Fc region" as appreciated by one of ordinary skill in the art comprises an amino acid sequence which differs from that of a native sequence Fc region by virtue of at least one "amino acid modification." Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 75 or 80% homology with a native sequence Fc region and/or with an Fc region of a parent polypeptide, and more preferably at least about 90% homology therewith, more preferably at least about 95% homology therewith, even more preferably, at least about 99% homology therewith.

The terms "Fc receptor" or "FcR" are used to describe a receptor that binds to the Fc region of an antibody. In one embodiment of the invention, FcR is a native sequence human FcR. In another embodiment, FcR, including human FcR, binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daron, Annu Rev Immunol, 15, 203-234 (1997); FcRs are reviewed in Ravetch and Kinet, Annu Rev Immunol, 9, 457-92 (1991); Capel et al., Immunomethods, 4, 25-34 (1994); and de Haas et al., J Lab Clin Med, 126, 330-41 (1995), Nimmerjahn and Ravetch 2006, Ravetch Fc Receptors in Fundemental Immunology, ed William Paul 5th Ed. each of which is incorporated herein by reference).

The term "native" or "parent" refers to an unmodified polypeptide comprising an Fc amino acid sequence. The parent polypeptide may comprise a native sequence Fc region or an Fc region with pre-existing amino acid sequence modifications (such as additions, deletions and/or substitutions).

Compositions

Within the scope of this invention is a composition that contains a suitable carrier and one or more of the agents described above, such as the non-sialylated IgG Fc variants. The composition can be a pharmaceutical composition that contains a pharmaceutically acceptable carrier or a cosmetic composition that contains a cosmetically acceptable carrier.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active compound. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate.

The above-described composition, in any of the forms described above, can be used for treating disorders characterized by inflammation. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment.

A pharmaceutical composition of this invention can be administered parenterally, orally, nasally, rectally, topically, or buccally. The term "parenteral" as used herein refers to subcutaneous, intracutaneous, intravenous, intrmuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acid, such as, but not limited to, oleic acid and its glyceride derivatives, are useful in the preparation of injectables, as are natural pharmaceutically acceptable oils, such as, but not limited to, olive oil or castor oil, polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, TWEENS or SPANS or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally comprise one or more excipients or diluents. In some preferred embodiments, the topical formulations include a material that would enhance absorption or penetration of the active agent(s) through the skin or other affected areas. The topical composition is useful for treating inflammatory disorders in the skin, including, but not limited to eczema, acne, rosacea, psoriasis, contact dermatitis, and reactions to poison ivy.

A topical composition contains a safe and effective amount of a dermatologically acceptable carrier suitable for application to the skin. A "cosmetically acceptable" or "dermatologically-acceptable" composition or component refers a composition or component that is suitable for use in contact with human skin without undue toxicity, incompatibility, instability, allergic response, and the like. The carrier enables an active agent and optional component to be delivered to the skin at an appropriate concentration(s). The carrier thus can act as a diluent, dispersant, solvent, or the like to ensure that the active materials are applied to and distributed evenly over the selected target at an appropriate concentration. The carrier can be solid, semi-solid, or liquid. The carrier can be in the form of a lotion, a cream, or a gel, in particular one that has a sufficient thickness or yield point to prevent the active materials from sedimenting. The carrier can be inert or possess dermatological benefits. It also should be physically and chemically compatible with the active components described herein, and should not unduly impair stability, efficacy, or other use benefits associated with the composition. The topical composition may be a cosmetic or dermatologic product in the form known in the art for topical or transdermal applications, including solutions, aerosols, creams, gels, patches, ointment, lotion, or foam.

Treatment Methods

The described invention provides methods for treating in a subject an inflammatory disorder. The term "inflammatory disorder" refers to a disorder that is characterized by abnormal or unwanted inflammation, such as an autoimmune disease. Autoimmune diseases are disorders characterized by the chronic activation of immune cells under non-activating conditions. Examples include psoriasis, inflammatory bowel diseases (e.g., Crohn's disease and ulcerative colitis), rheumatoid arthritis, psoriatic arthritis, multiple sclerosis, lupus, type I diabetes, primary biliary cirrhosis, and transplant.

Other examples of inflammatory disorders that can be treated by the methods of this invention include asthma, myocardial infarction, stroke, inflammatory dermatoses (e.g., dermatitis, eczema, atopic dermatitis, allergic contact dermatitis, urticaria, necrotizing vasculitis, cutaneous vasculitis, hypersensitivity vasculitis, eosinophilic myositis, polymyositis, dermatomyositis, and eosinophilic fasciitis), acute respiratory distress syndrome, fulminant hepatitis, hypersensitivity lung diseases (e.g., hypersensitivity pneumonitis, eosinophilic pneumonia, delayed-type hypersensitivity, interstitial lung disease (ILD), idiopathic pulmonary fibrosis, and ILD associated with rheumatoid arthritis), and allergic rhinitis. Additional examples also include myasthenia gravis, juvenile onset diabetes, glomerulonephritis, autoimmune throiditis, ankylosing spondylitis, systemic sclerosis, acute and chronic inflammatory diseases (e.g., systemic anaphylaxia or hypersensitivity responses, drug allergies, insect sting allergies, allograft rejection, and graft-versus-host disease), and Sjogren's syndrome.

A "subject" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental, non-human animal or animal suitable as a disease model.

A subject to be treated for an inflammatory disorder can be identified by standard diagnosing techniques for the disorder. Optionally, the subject can be examined for the level or percentage of one or more of cytokines or cells a test sample obtained from the subject by methods known in the art. If the level or percentage is at or below a threshold value (which can be obtained from a normal subject), the subject is a candidate for treatment described herein. To confirm the inhibition or treatment, one can evaluate and/or verify the level or percentage of one or more of the above-mentioned cytokines or cells in the subject after treatment.

"Treating" or "treatment" refers to administration of a compound or agent to a subject who has a disorder with the purpose to cure, alleviate, relieve, remedy, delay the onset of, prevent, or ameliorate the disorder, the symptom of the disorder, the disease state secondary to the disorder, or the predisposition toward the disorder.

An "effective amount" or "therapeutically effective amount" refers to an amount of the compound or agent that is capable of producing a medically desirable result in a treated subject. The treatment method can be performed in vivo or ex vivo, alone or in conjunction with other drugs or therapy. A therapeutically effective amount can be administered in one or more administrations, applications or dosages and is not intended to be limited to a particular formulation or administration route.

The agent can be administered in vivo or ex vivo, alone or co-administered in conjunction with other drugs or therapy, i.e., a cocktail therapy. As used herein, the term "co-administration" or "co-administered" refers to the administration of at least two agents or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In an in vivo approach, a compound or agent is administered to a subject. Generally, the compound or agent is suspended in a pharmaceutically-acceptable carrier (such as, for example, but not limited to, physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds/agents available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) can increase the efficiency of delivery, particularly for oral delivery.

Example 1

Methods and Materials

This example describes general methods and materials used in Examples 2-7.

Mice

Wild-type C57BL/6 mice were purchased from Jackson Laboratories. $SIGNR^{-/-}$ mice were provided by A. McKenzie. CD11c-DC-$SIGN^{+}$ transgenic mice were provided by T. Sparwasser. hDC-SIGN BAC transgenic mice in a $SIGNR1^{-/-}$ background were generated in inventors' laboratory as previously described. KRN TCR C57BL/6 mice (gifts from D. Mathis and C. Benoist) were bred with NOD mice to generate K/B×N mice. Blood from K/B×N mice (6-12 weeks of age) were collected and serum containing arthritogenic antibodies pooled together. Passive transfer of 200 μL K/B×N serum by i.v. injection to naïve mice (8-12 weeks of age) induced arthritis. Inflammation was scored 0-3 for each paw and added together for a total clinical score per individual mouse.

Recombinant Fc Preparation

IDEC-114, a recombinant source of full-length human IgG1 monoclonal antibody, was digested with papain overnight at 37° C. to cleave the Fab and Fc fragments. Following digest, the reaction was stopped by the addition 2.5 mg/mL iodoacetamide. To separate cleaved fragments from undigested antibody, samples were passed over a HiPrep 26/60 S-200HR size-exclusion column (GE HEALTH- CARE). The Fc fragment was subsequently purified with protein G agarose beads. Sample purity was verified by coomassie brilliant blue staining of SDS-polyacrylamide gels. Alternatively, recombinant Fcs were produced by the transient transfection of human IgG1 Fc-expressing plasmids into 293T cells followed by ammonium sulfate precipitation of supernatant fractions and protein G purification. The genetic sequence coding for the Fc region of human IgG1 was amplified from 4-4-20 IgG1 by standard PCR protocols and ligated into pSecTag2 (INVITROGEN). Point mutations were introduced into the Fc coding sequence by standard site-directed mutagenesis techniques and verified by DNA sequencing. PCR primers for the Phe to Ala substitution at position 241 (FA241) were 5'-ggggaccgtcagtcgccctcttccccccaa-3' (SEQ ID NO: 4) and 5'-ttgggggggaagagggcgactgacggtcccc-3' (SEQ ID NO: 5). Protein expression and purity was confirmed by immunoblotting with anti-human Fc antibodies and/or coomassie brilliant blue staining of SDS-polyacrylamide gels.

Two-Step in Vitro Sialylation Reaction

Following purification, 10-50 mg/mL Fc fragments were buffer exchanged into a galactosylation reaction buffer (50 mM MOPS, pH 7.2; 20 mM $MnCl_2$) and incubated overnight at 37° C. with 50 mg UDP-galactose and 0.75 U β1,4-galatosyltransferase. Galactosylation was confirmed by lectin blots using ECL to recognize terminal galactose residues. Galactosylated Fcs were then buffer exchanged into a sialylation reaction buffer (100 mM MOPS, 0.2 mg/mL BSA, 0.5% Triton X-100, pH 7.4) and incubated overnight at 37° C. with 50 mg CMP-sialic acid and 0.75 U α2,6-sialyltransferase. Sialylation was confirmed by lectin blots using SNA to recognize terminal sialic acid residues with an α2-6 linkage.

Adoptive Transfer of Bone Marrow-Derived Macrophages

Bone marrow cells were flushed from tibias and femurs of DC-SIGNtg or SIGNR1$^{-/-}$ mice, and seeded in non-tissue culture treated 10-cm plates in RPMI 1640 growth media supplemented with 10% FBS, 1% Pen/Strep, IL-3 (5 ng/mL, PEPROTECH), and M-CSF (5 ng/mL, PEPROTECH). Following overnight incubation at 37° C., non-adherent cells were recovered and transferred to non-tissue culture treated 10-cm plates with IL-3/M-CSF-supplemented RPMI growth media, and cultured for 5-7 days at 37° C. Mature macrophages were trypsinized and plated in 6-well plates at a density of $2\times10^6$ cells/well, and allowed to attach overnight. The next day macrophages were pulsed with the indicated recombinant Fc preparation for 30 min at 37° C. The cells were recovered, washed with cold PBS, and $1\times10^6$ cells were administered i.v. to wild-type C57BL/6 mice. One hour post-injection, recipient mice were challenged with K/B×N sera.

Expression and Purification of Soluble Human DC-SIGN

A plasmid containing the cDNA sequence of the extracellular domain (ECD) of human DC-SIGN was provided by K. Drickamer. The coding sequence for DC-SIGN ECD was modified to introduce an N-terminal strep tag by standard PCR techniques and ligated to pET28b(+). pET28b-strepDCSIGN was transformed into *E. coli* strain BL21/DE3 and grown in 3 L of TB growth medium at 37° C. until bacteria culture reached $OD_{600}$ 0.7-0.8. Protein expression was induced by the addition of 100 mg/L of IPTG and cultures incubated at 37° C. for 3.5 h. Bacteria were pelleted by centrifugation at 4000×g for 10 min at 4° C. Bacteria pellets were resuspended in 10 mM Tris-HCl, pH 7.8, and lysed by sonication. Inclusion bodies were pelleted by centrifugation at 10,000×g for 15 min at 4° C. and solubilized in 100 mL of 6 M guanidine-HCl; 100 mM Tris-HCl, pH 7.8; 0.2% TRITON X-100. Particulate matter was removed by centrifugation at 20,000×g for 30 min at 4° C., and the supernatant fraction was dialyzed against 250 mM NaCl; 25 mM Tris-HCl, pH 7.8; 25 mM $CaCl_2$. After dialysis, insoluble precipitates were removed by centrifugation at 20,000×g for 30 min at 4° C., and the supernatant fraction applied to a strep-tactin resin (NOVAGEN) to pull down strep-tagged DC-SIGN ECD. Bound proteins were eluted from resin with elution buffer supplied by manufacturer (NOVAGEN). Fractions were analyzed by SDS-PAGE and positive fractions combined and loaded onto a mannose-agarose column to select for active receptors. DC-SIGN ECD was eluted with 250 mM NaCl; 25 mM Tris-HCl, pH 7.8; 5 mM EDTA. Fractions were analyzed by SDS-PAGE.

Surface Plasmon Resonance

To determine the interaction between various recombinant Fc preparations to soluble hDC-SIGN or hFcγRs, steady-state affinity measurements were recorded on a Biacore T100 sensor. Receptors, diluted to 20-50 μg/mL in NaOAc pH 5.0, were immobilized on CMS chips at high density (2000 RU) by standard amine coupling. For hDC-SIGN interactions, injections were performed at a flow rate of 20 μL/min with commercially available HBS-P+ buffer adjusted to pH 9.0 and supplemented with 2 mM $CaCl_2$ and 500 mM NaCl. For hFcγRs interactions, injections were performed at a flow rate of 20 μL/min with commercially available HBS-EP+ buffer. Surfaces were regenerated with a short pulse of 50 mM NaOH. $K_d$ values were calculated after subtraction of background binding to a control flow cell using Biacore Evaluation software.

RT-PCR

Total RNA was extracted from bone marrow-derived macrophages using RNeasy Mini kit (QIAGEN). One microgram of total RNA was used to analyze IL-33 mRNA expression by RT-PCR using OneStep RT-PCR kit (QIAGEN). Expression of GAPDH served as a loading control. PCR primers for mIL-33 were 5'-gaagatcccaacagaagacc-3' (SEQ ID NO: 6) and 5'-ttccggaggcgagacgtcac-3'(SEQ ID NO: 7); and mGAPDH were 5'-gccgcctggagaaacctgc-3' (SEQ ID NO: 8) and 5'-tgaggtccaccaccctgttg-3' (SEQ ID NO: 9). The PCR conditions were 94° C. for 30 s; 55° C. for 30 s; 72° C. for 60 s×35 cycles (IL-33) or 25 cycles (GAPDH).

Example 2

α2,6-Linked Sialic Acid Conferred DC-SIGN Binding Activity to Recombinant Human IgG1 Fc A minor population of antibodies in IVIG preparations suppresses autoantibody-induced inflammation. These antibodies, containing terminal α2,6-linked sialic acid on the Fc glycan, mediate an anti-inflammatory response by binding to SIGNR1 on marginal zone macrophages or its human orthologue, DC-SIGN, on myeloid cells.

To study the interaction of sFc to DC-SIGN, a soluble form of the extracellular domain of DC-SIGN (DC-SIGN ECD) was purified from bacteria and immobilized on CMS chips. sFc was prepared from full-length IDEC-114 antibodies and sialylated in vitro (FIG. 1*b*), and was specifically bound to DC-SIGN-conjugated surface (FIG. 1*a*). Steady-state affinity measurements were carried out and the $K_D$ value for this interaction was calculated as $\sim1.3\times10^{-6}$ M (FIG. 1*c*.). In contrast, an asialylated glycoform of IDEC-114 Fc showed no binding activity to DC-SIGN suggesting that sialylation induces a conformational change in on the Fc backbone to reveal a DC-SIGN binding site.

As shown in FIG. 1*a*, it was found that recombinant a2,6-sFc bound to soluble DC-SIGN as measured by surface plasmon resonance (SPR). Fcs were prepared by papain cleavage of full-length human monoclonal IgG1 antibody (IDEC-114) followed by in vitro galactosylation and sialylation reactions. The SPR sensorgrams for antibody binding to immobilized DC-SIGN are shown for sialylated and galactosylated glycoforms of hIgG1 Fcs as described above in Example 1. It was found that Fc concentrations flowed over DC-SIGN ECD range from 3-0.8 μM. As shown in FIG. 1*b*, lectin blot with SNA confirmed attachment of sialic acid with 2,6-linkage on Fc (top panel); coomassie stained loading controls was shown in bottom panel. Steady-state $K_D$ measurement of sFc binding to DC-SIGN (as shown in a.) was calculated by Biacore Evaluation software.

Example 3

Mutations Disrupting Fc-Glycan Interactions Conferred DC-SIGN Binding Activity to Recombinant Human IgG1 Fc The core oligosaccharide chain attached to $Asn^{297}$ makes extensive noncovalent interactions with the amino acid backbone of the Fc. Conformational changes in the Fc induced by different sugar residues attached to the core glycan are mediated by these protein-carbohydrate interactions. Alanine substitutions that abolish key contact points between the Fc backbone and glycan residues appear to impart DC-SIGN binding activity.

Figure 2:
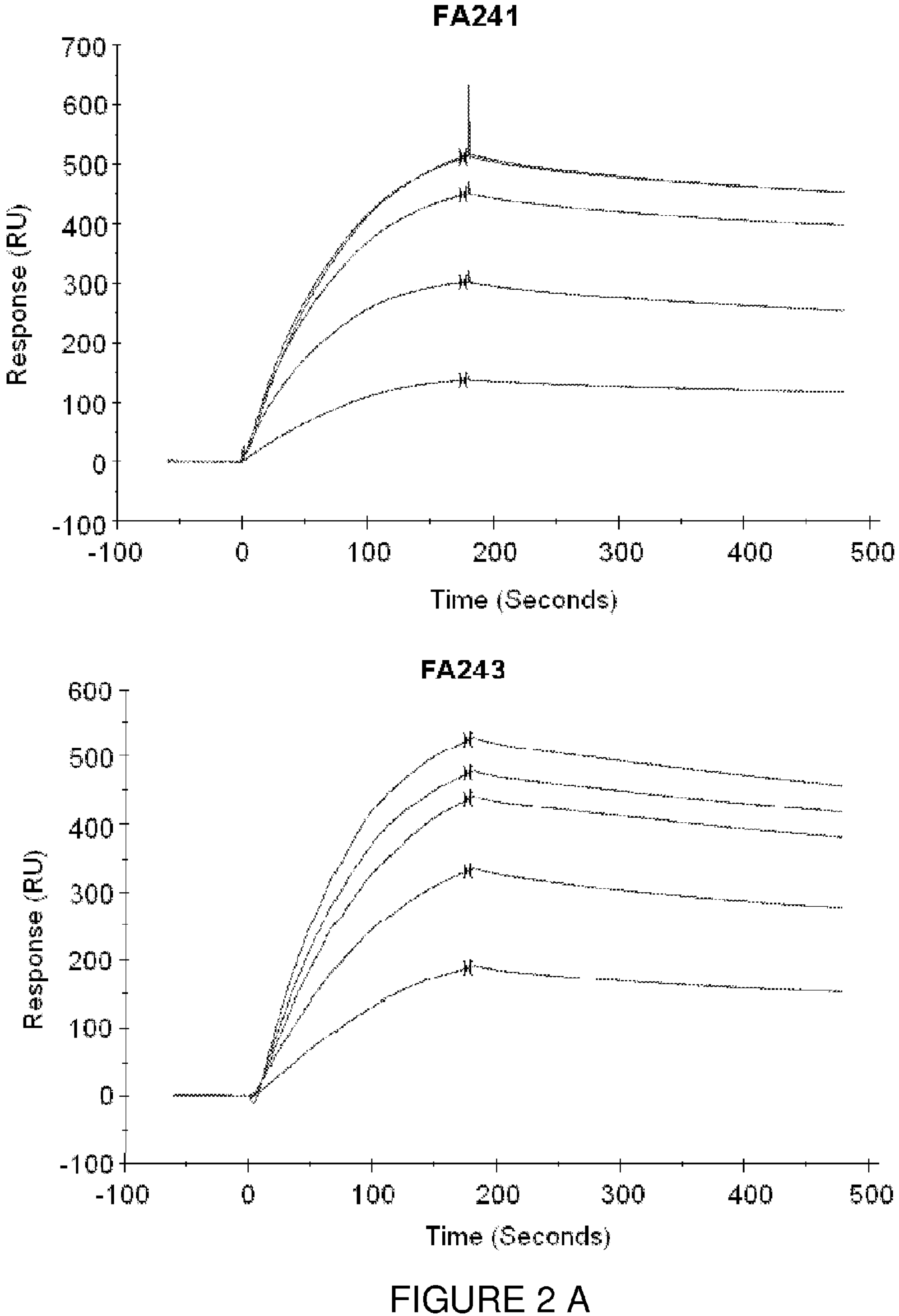
FIGS. 2a-b are diagrams and photographs showing that disrupting Fc-glycan interactions conferred DC-SIGN binding activity to recombinant human IgG1 Fc.
Figure 2:
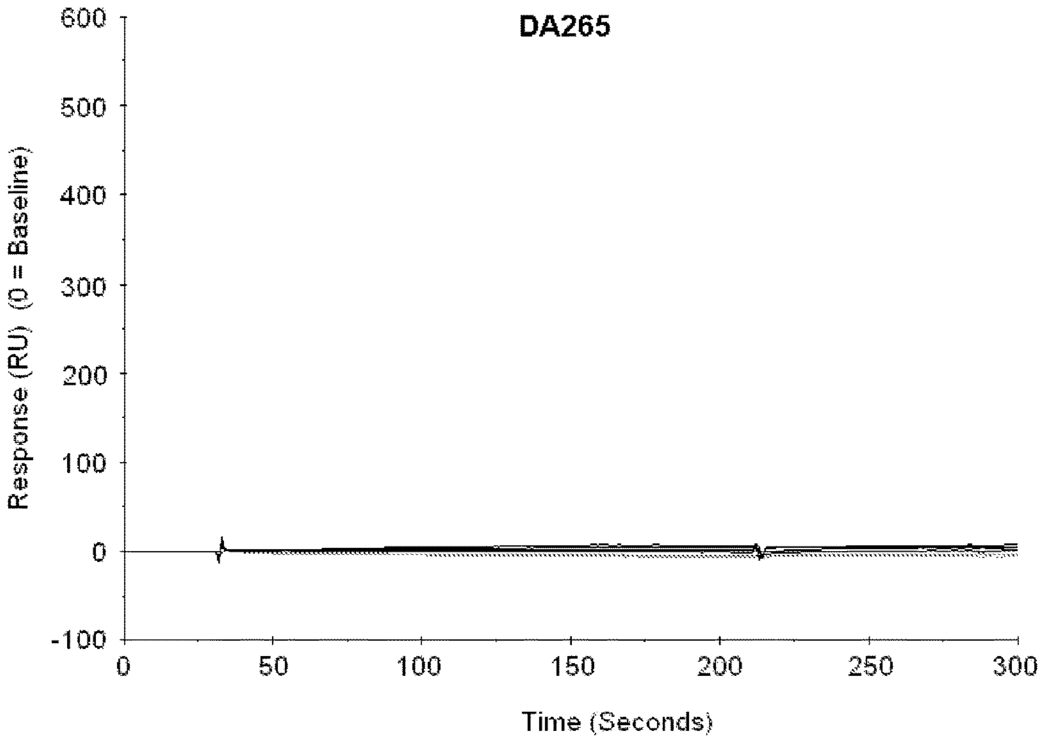
Figure 2:
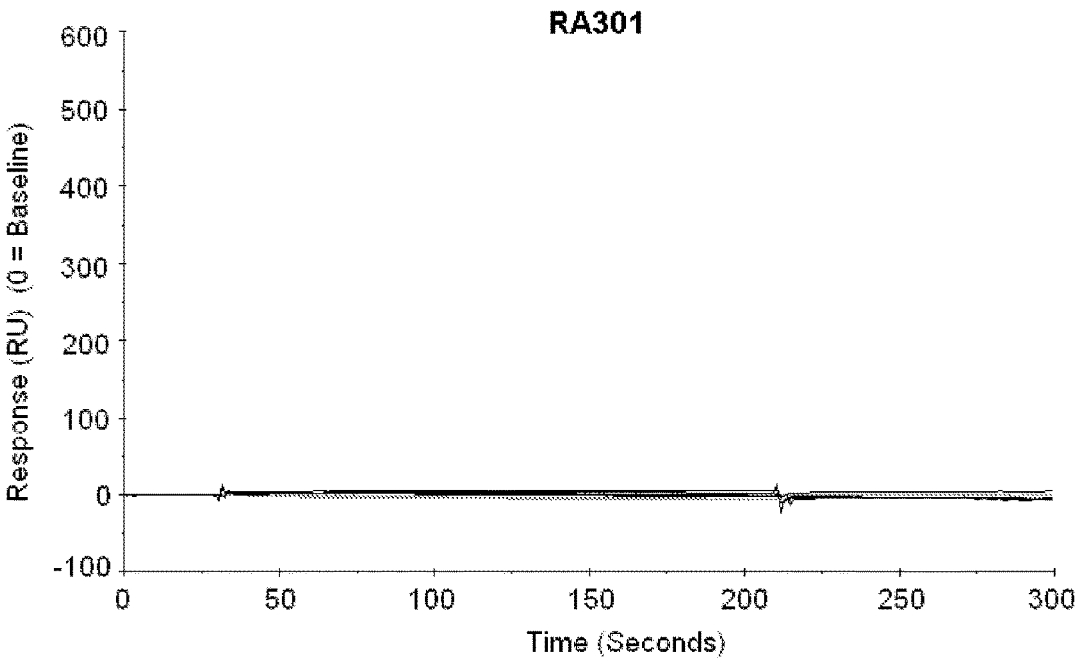
Figure 2:
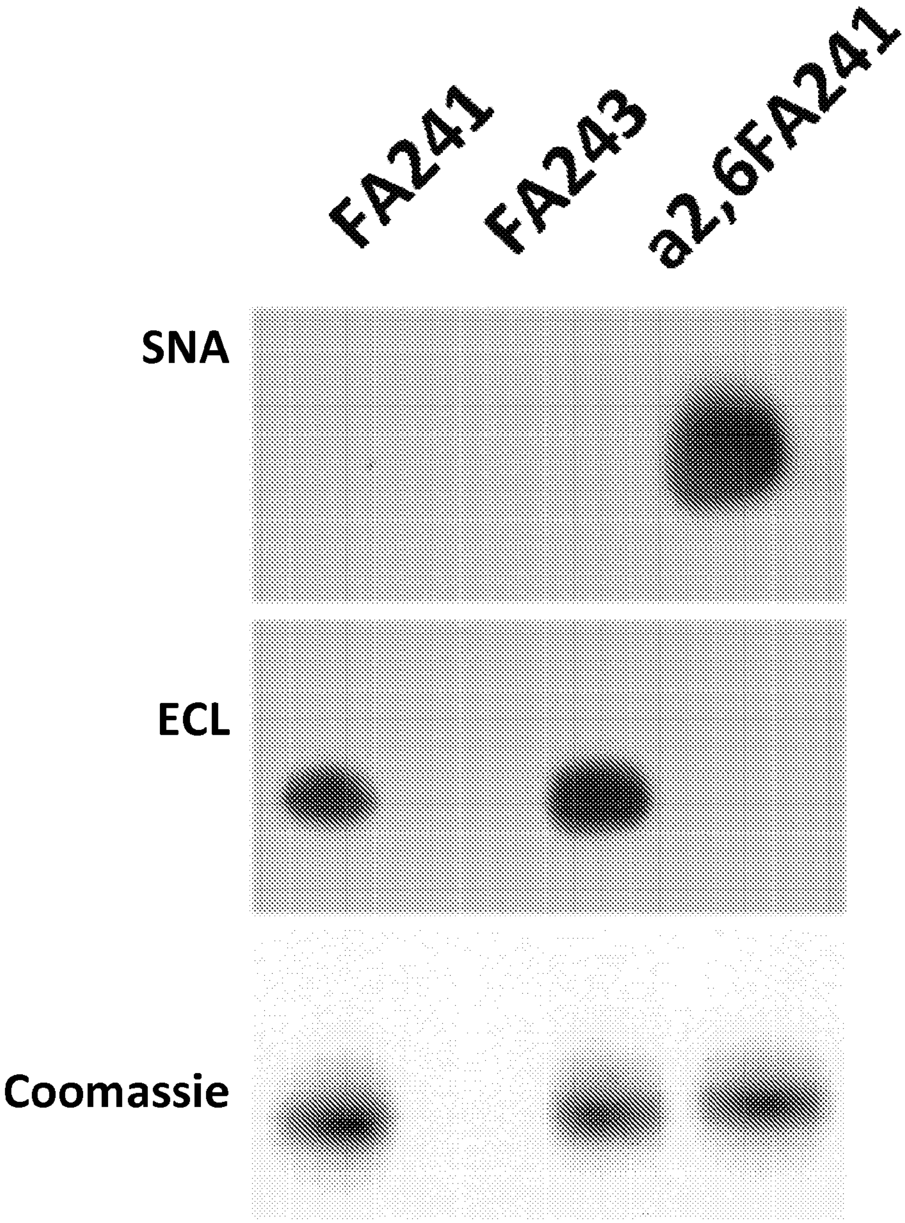

As shown in FIG. 2A, FA241 and FA243 mutations exhibit DC-SIGN binding activity without in vitro enzymatic processing. Apparent $K_D$ values range from $6\times10^{-7}$ M for FA241 to $3\times10^{-7}$ M for FA243. Previous reports indicate that these mutations increase sialylation of antibodies, presumably by making the glycan more accessible to glycosyltransferases, when expressed in mammalian cells. To verify this, a lectin blot was performed to determine if FA241 and FA243 binding to DC-SIGN is due to increased sialylation of transiently expressed proteins. As shown in FIG. 2B, SNA blots did not detect terminal sialic acid residues in purified FA241 and FA243 indicating that DC-SIGN interaction was independent of sialic acid modification.

More specifically, residues F241, F243, D265, and R301 along the amino acid backbone of IgG1 Fc were replaced with alanine to disrupt noncovalent interactions with oligosaccharide residues. Fcs were expressed and purified from 293T cells and analyzed for DC-SIGN binding activity with surface plasmon resonance as described above. It was found Fcs bearing mutations FA241 or FA243 exhibited increased affinity to DC-SIGN relative to affinity measurements for sFc (FIG. 1*a*). Lectin blots with ECL (FIG. 1*b*, middle panel) and SNA (top panel) were carried out to determine terminal sugar moieties on Fcs purified from 293T cells. As a positive control for sialylated Fcs, FA241 was sialylated in vitro as described in FIG. 1*a*. Coomassie stained loading controls shown in bottom panel of FIG. 1*b*.

Example 4

FA241 Mutation in hIgG1 Fc Recapitulated Anti-Inflammatory Activity of α2,6 sFc

If the FA241 and FA243 mutations mimic the DC-SIGN binding activity of sFc, assays were carried out to examine if these mutations could replicate the anti-inflammatory activity of sFc in vivo. Age- and sex-matched $SIGNR1^{-/-}$ and $hDC\text{-}SIGN^{+}/SIGNR1^{-/-}$ mice were challenged with arthritogenic K/B×N sera and treated with sFc, FA241, or FA243 at an effective dose of 0.033 g/kg. Consistent with previous findings, sFc suppressed footpad swelling in $DC\text{-}SIGN^{+}$ mice but not in $SIGNR1^{-/-}$. Similarly, FA241 demonstrated comparable anti-inflammatory activity to that of sFc in $hDC\text{-}SIGN^{+}/SIGNR1^{-/-}$ mice. Mice administered FA243 showed no reduction in joint inflammation. These findings suggest that recombinant Fcs bearing an $F_{241}A$ mutation (FA241) recapitulates the DC-SIGN binding and anti-inflammatory activity of sFc in the absence of sialic acid modification.

Figure 3:
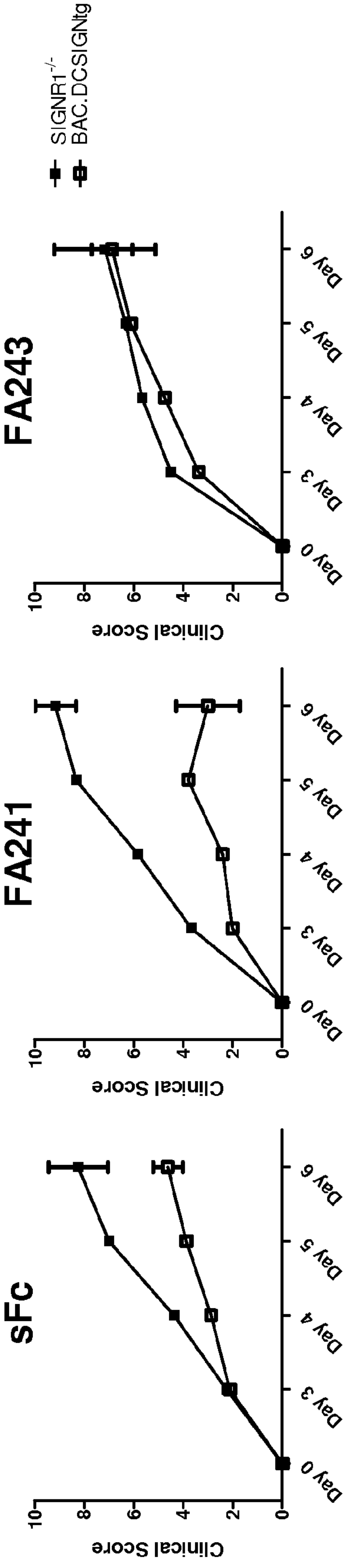
FIG. 3 is as set of diagrams showing that the FA241 mutation in hIgG1 Fc recapitulates anti-inflammatory activity of α2,6 sFc.

As showing in FIG. 3, $hDC\text{-}SIGN^{+}/SIGNR1^{-/-}$ (white squares) and $SIGNR1^{-/-}$ (black squares) mice were administered 0.7 mg/mouse of sFc, FA241, or FA243 by i.v. injection. Mice were subsequently challenged with K/B×N sera 1 h later. Footpad swelling was monitored and scored over several days. As previously reported, anti-inflammatory activity of sFc is DC-SIGN-dependent (left panel). FA241 also suppressed arthritic inflammation in K/B×N challenged mice in a DC-SIGN-dependent manner. FA243 did not reduce significantly footpad swelling at day 6. Means and SEM of clinical scores of 4-5 mice per group are plotted on Day 6.

Example 5

Characterizing Requirements for FA241 Anti-Inflammatory Activity

To identify the determinants for the anti-inflammatory activity of FA241, bone marrow-derived macrophages (BMMΦ) from $CD11c.DC\text{-}SIGN^{+}$ and $SIGNR1^{-/-}$ mice were stimulated with FA241 or other Fc preparations and transferred to WT C57BL/6 recipient mice challenged with K/B×N sera.

Figure 4:
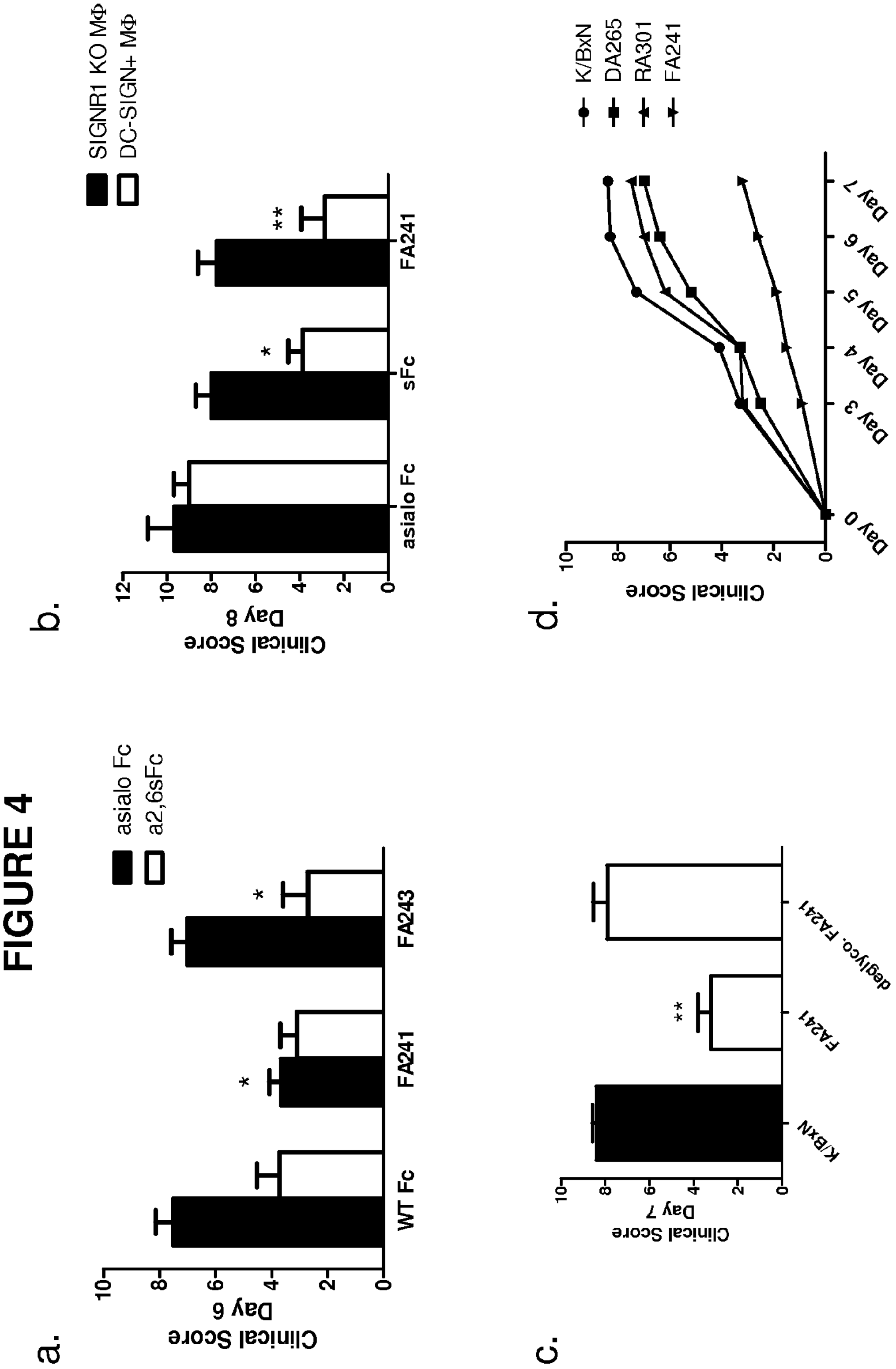
FIGS. 4a-d are diagrams showing characterizing requirements for FA241 anti-inflammatory activity.

Briefly, bone marrow-derived macrophages from $CD11c.DC\text{-}SIGN^{+}$ and $SIGNR1^{-/-}$ mice were cultured in IL-3 (5 ng/mL) and M-CSF (5 ng/mL) for 5-7 days. As shown FIG. 4, $DC\text{-}SIGN^{+}$ BMMΦ were pulsed with 0.5 mg/mL asialylated (black bars) or sialylated (white bars) glycoforms of indicated Fc preparations. Fc-treated BMMΦ were transferred to WT C57BL/6 recipient mice followed by K/B×N challenge. As shown in FIG. 4*b* $SIGNR1^{-/-}$ (black bars) and $DC\text{-}SIGN^{+}$ (white bars) BMMΦ were pulsed with 0.5 mg/mL of indicated Fc preparation and transferred to WT C57BL/6 recipient mice followed by K/B×N challenge. Similarly, $DC\text{-}SIGN^{+}$ BMMΦ were pulsed with either 0.5 mg/mL of FA241 or deglycosylated FA241 (FIG. 4*c*, white bars) or PBS (FIG. 4*c* black bar) and transferred to WT C57BL/6 recipient mice followed by K/B×N challenge. FA241 was deglycosylated with PNGase F and glycan removal confirmed by lectin blotting. $DC\text{-}SIGN^{+}$ BMMΦ were pulsed with indicated asialylated Fc preparation or PBS (FIG. 4*d*, black circle) and transferred to WT C57BL/6 recipient mice followed by K/B×N challenge. In all cases, footpad swelling was monitored and scored over several days. Means and SEM of clinical scores of 4-5 mice per group are plotted. *$P<0.05$, as determined by an analysis of variance (ANOVA) test, followed by a Tukey post hoc test.

As shown in FIG. 4A, asialylated or sialylated FA241 preparations were equally effective at suppressing joint inflammation compared to sFc. WT Fc preparations, however, required α2,6-linked sialic acid since $DC\text{-}SIGN^{+}$ BMMΦ pulsed with asialylated WT Fc did not transfer protection to recipient mice. Corresponding with results showed in FIG. 3, both sFc and FA241 required DC-SIGN expression on BMMΦ to transfer protection (FIG. 4B). Though FA241 does not require sialic acid to transfer protection, deglycosylation with PNGase F abrogated the anti-inflammatory properties of FA241 (FIG. 4C) suggesting that the Fc glycan is still necessary. Furthermore, to show that the observed anti-inflammatory activity is specific for the $F_{241}$A mutation, DC-SIGN$^+$ BMMΦ were pulsed with Fcs bearing alternative mutations that do not confer enhanced DC-SIGN binding. Only FA241-stimulated BMMΦ protected K/B×N challenged recipient mice.

Example 6

FA241 Mutation Increased Fcγ Receptor Binding

If an alanine substitution at position 241 induces a conformational change in the Fc, then perhaps affinity towards human Fcγ receptors will be altered. It was previously reported that sialylation reduces the affinity of IgGs to FcγRs, consequently attenuating ADCC activity in vivo.

Recombinant IgG1 Fc's binding to soluble FcγRs was measured by surface plasmon resonance (SPR). Fcs were prepared in the manner described above. The SPR sensorgrams for antibody binding to immobilized $hFc\gamma RIIA_{131R}$ and hFcγRIIB are shown in FIG. 5 for asialylated and sialylated glycoforms of WT hIgG1 Fc and for asialylated FA241 Fc.

Figure 5:
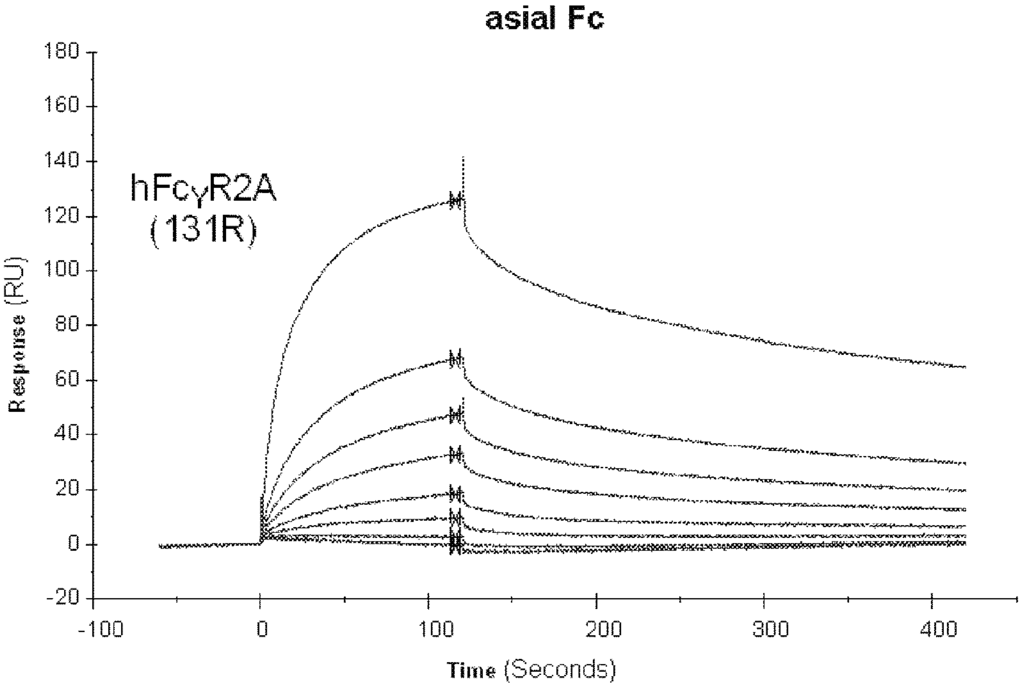
FIG. 5 is a set of diagrams showing that FA241 mutation increased Fcγ receptor binding.
Figure 5:
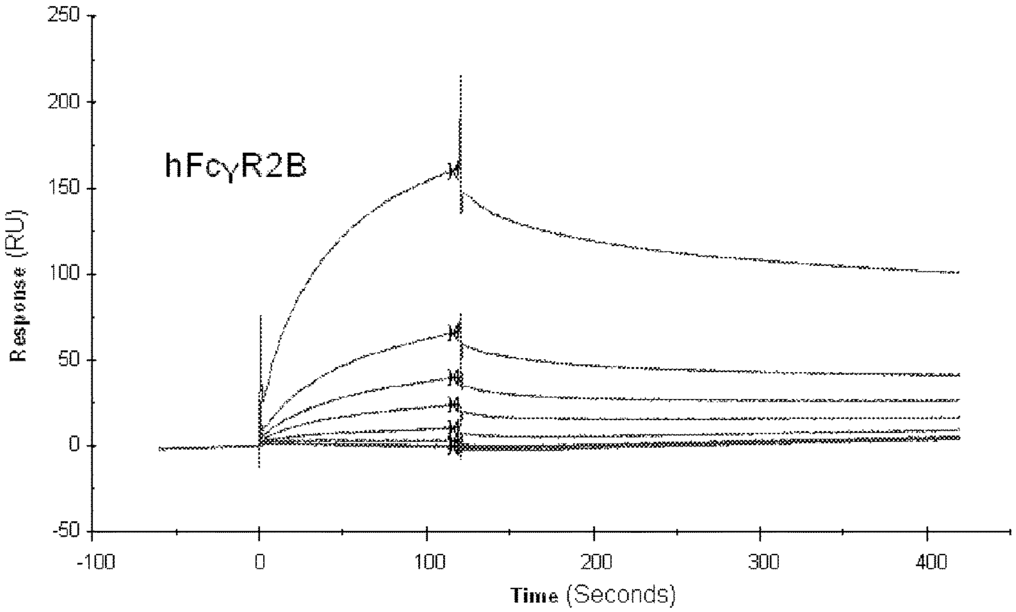
Figure 5:
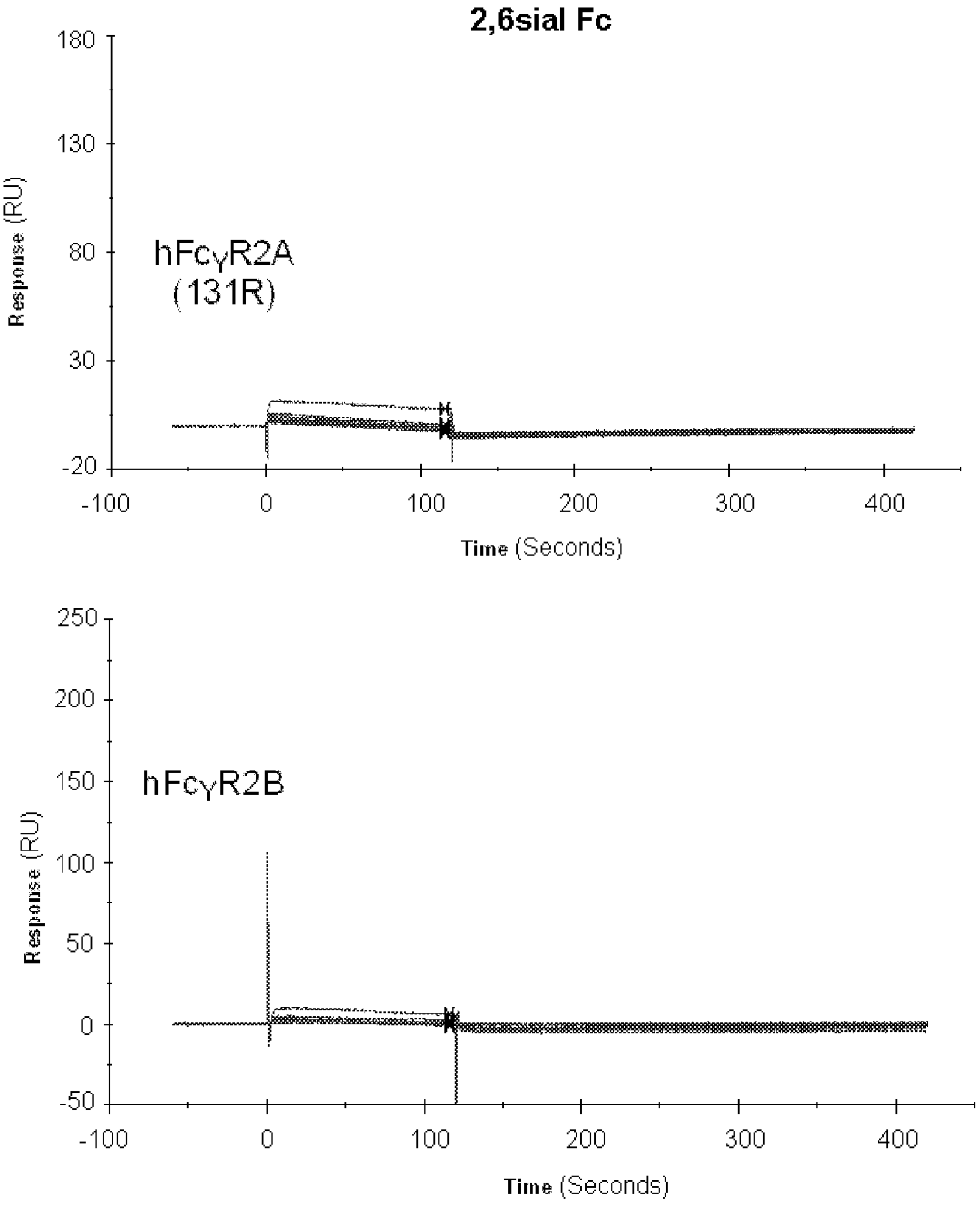
Figure 5:
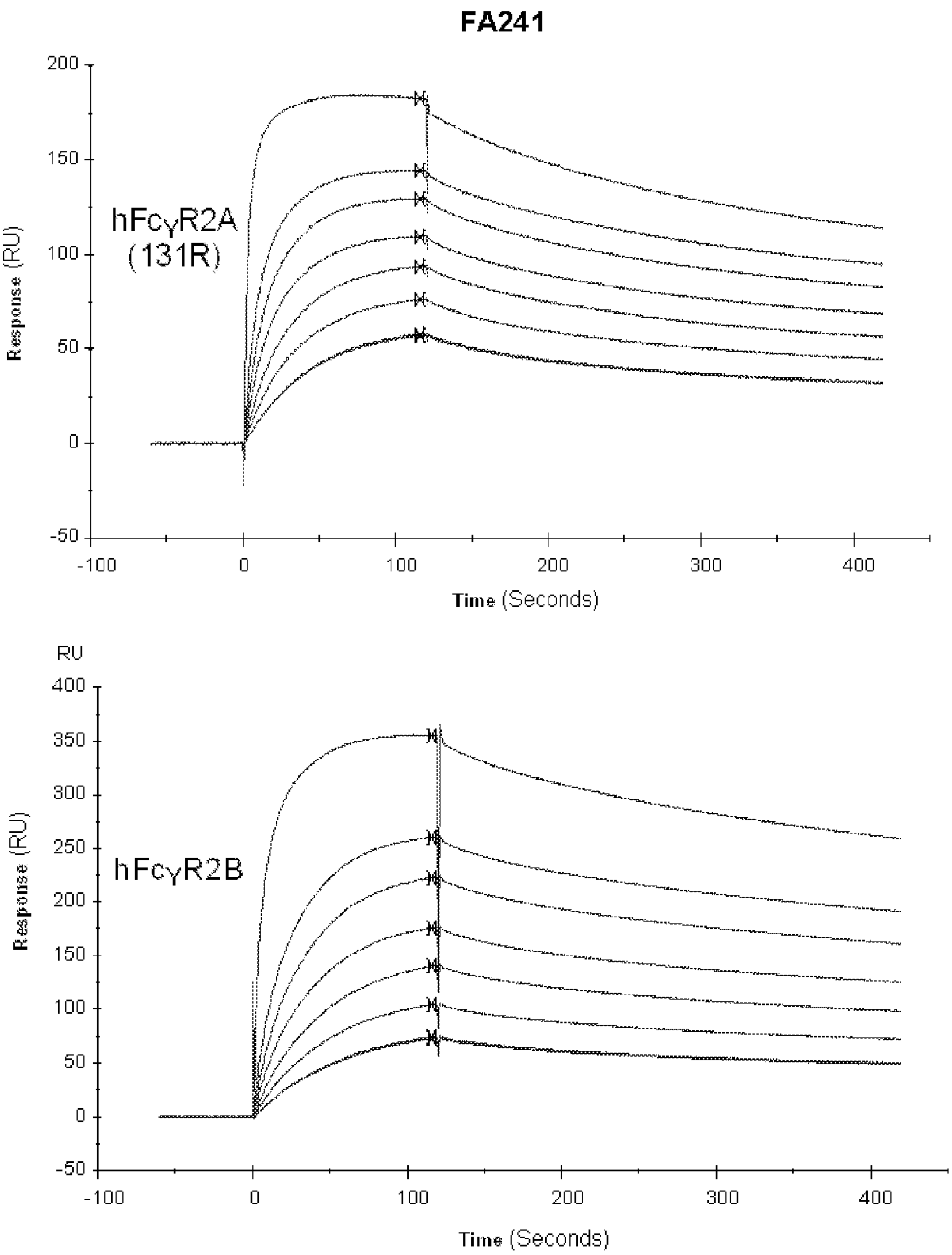

As shown in FIG. 5, asialylated glycoforms of WT Fc bound to hFcγRIIA and RIIB with an observed $K_D$ value of ~2-3×$10^{-5}$ M. sFc, however, did not appear to bind either hFcγRIIA or RIIB Surprisingly, FA241 appears to bind both hFcγRIIA and RIIB with an order of magnitude greater affinity ($K_D$=~2×$10^{-6}$ M).

Example 7

IL-33 mRNA Induction in Bone Marrow-Derived Macrophages by FA241 sFc induce a $T_H$2-dependent anti-inflammatory pathway that requires IL-4 secretion from an FcεRI$^+$ leukocyte population, likely basophils, to upregulate FcγRIIB on regulatory macrophages. Administration of IL-33 in vivo or in vitro stimulates basophils to release stores of IL-4. IL-33 mRNA expression is upregulated in spleens of WT C57BL/6 mice treated with sFc or IVIG, but not in SIGNR1$^{-/-}$ mice. This suggests that sFc may induce IL-33 expression in SIGNR1$^+$ or DC-SIGN$^+$ cells. In this example, assays were carried out and show that stimulating DC-SIGN$^+$ BMMΦ with FA241 appears to upregulate IL-33 expression.

More specifically, bone marrow-derived macrophages from CD11c.DC-SIGN$^+$ and SIGNR1$^{-/-}$ mice were cultured in the manner described above. BMMΦ were seeded onto 12-well plates in serum-free RPMI media and allowed to adhere overnight at 37° C. Next day, cells were pulsed with 0.5 mg/mL of indicated Fc in serum-free RPMI media for 1 h (FIG. 6*a*.) or 4 h (FIG. 6*b*.) at 37° C. mRNA was harvested from cells at specified time points and 1 μg total RNA used for RT-PCR amplification of IL-33 mRNA (top panels). GAPDH amplification served as a loading control (bottom panels). Plasmid co-expressing DA265 Fc and human sialyltransferase (ST6Gal1) were transfected into 293T cells yielding highly sialylated recombinant Fc (ST6-DA265).

Figure 6:
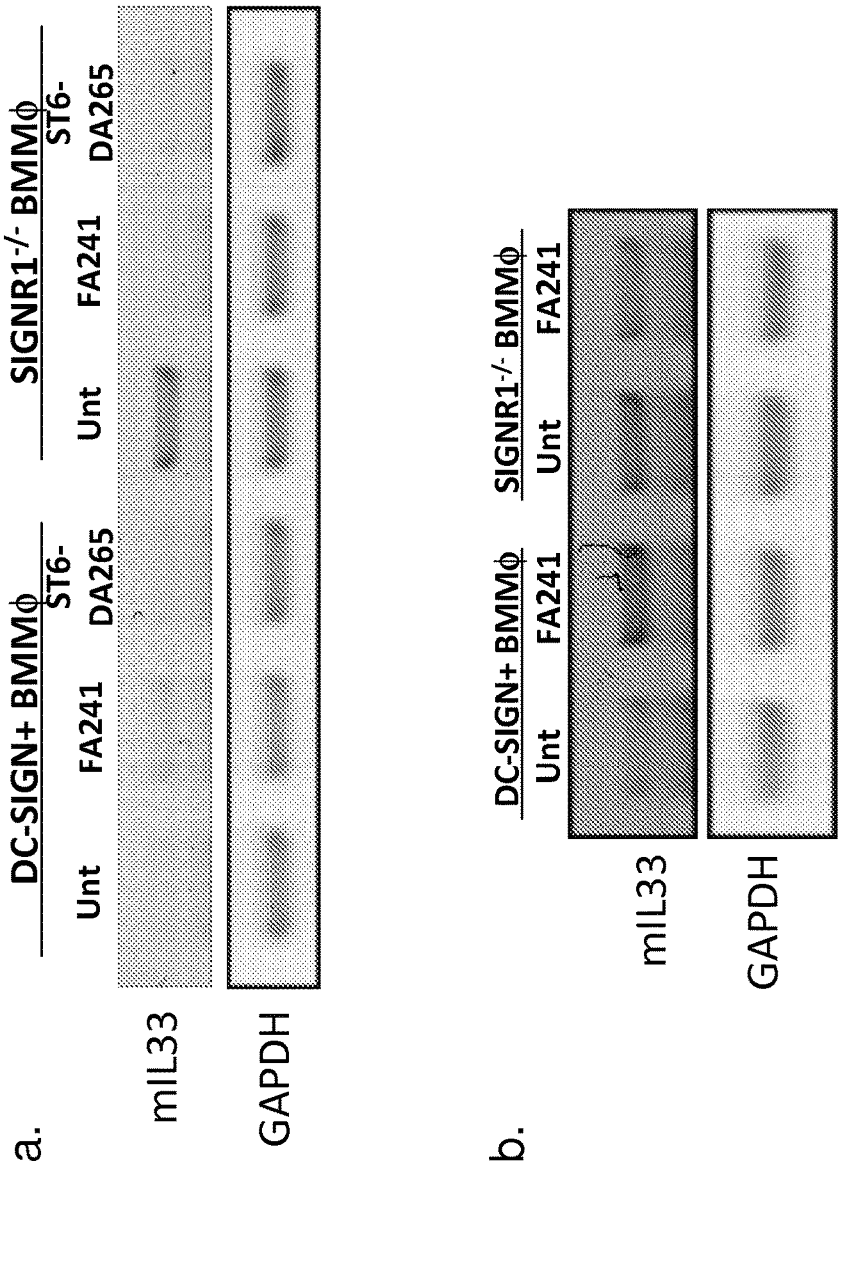
FIGS. 6a-b are photographs showing IL-33 mRNA induction in bone marrow-derived macrophages by FA241.

As shown in FIG. 6, stimulating DC-SIGN$^+$ BMMΦ with FA241 appears to upregulate IL-33 expression. Despite greater basal expression levels of IL-33 compared to DC-SIGN$^+$ BMMΦ, SIGNR1$^{-/-}$ BMMΦ downregulated IL-33 mRNA expression in response to FA241 treatment.

The foregoing example and description of the preferred embodiments should be taken as illustrating, rather than as limiting the present invention as defined by the claims. All publications cited herein are hereby incorporated by reference in their entirety. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims.

What is claimed:

1. An isolated polypeptide comprising a modified sequence that comprises SEQ ID NO: 2 and is at least 75% identical to the Fc region of an IgG (IgG Fc region), wherein the modified sequence is free of sialylation, and the polypeptide has an ability to bind to a Fc receptor and an anti-inflammatory activity that is higher than that of a parent polypeptide, said parent polypeptide comprising the IgG Fc region.

2. The isolated polypeptide of claim 1, wherein the isolated polypeptide has an ability to bind to Dendritic Cell-Specific Intercellular adhesion molecule-3-Grabbing Non-integrin (DC-SIGN).

3. The isolated polypeptide of claim 1, wherein the isolated polypeptide has an ability to bind to hFcγRIIA or hFcγRIIB.

4. The isolated polypeptide of claim 3, wherein the isolated polypeptide has an ability to bind to hFcγRIIA or hFcγRIIB at a $K_D$ of $2\times10^{-5}$ M or lower.

5. The isolated polypeptide of claim 1, wherein the modified sequence consists essentially of SEQ ID NO: 2.

6. A pharmaceutical formulation comprising (i) the polypeptide of any of claims 1, 2-4, and 5, and (ii) a pharmaceutically acceptable carrier.

7. A method of treating an inflammatory disease, comprising administering to a subject in need thereof a therapeutically effective amount of the polypeptide of any of claims 1, 2-4, and 5.

* * * * *

UNITED STATES PATENT AND TRADEMARK OFFICE

CERTIFICATE OF CORRECTION

PATENT NO. : 9,587,025 B2
APPLICATION NO. : 14/368701
DATED : March 7, 2017
INVENTOR(S) : Jeffrey V. Ravetch et al.

It is certified that error appears in the above-identified patent and that said Letters Patent is hereby corrected as shown below:

In the Specification

At Column 1, Line number 17, delete "The invention disclosed herein was made, at least in part, with Government support under Grant No. NIH AI035875 from the National Institutes of Health. Accordingly, the U.S. Government has certain rights in this invention." and replace with -This invention was made with government support under NIH AI035875 awarded by the NIH. The government has certain rights in the invention.-

Signed and Sealed this
Twenty-fifth Day of July, 2017

Joseph Matal

Joseph Matal
*Performing the Functions and Duties of the*
*Under Secretary of Commerce for Intellectual Property and*
*Director of the United States Patent and Trademark Office*